(12) United States Patent
Walsh et al.

(10) Patent No.: US 9,638,676 B2
(45) Date of Patent: May 2, 2017

(54) GC COLUMN CONNECTION WITH A PLANAR CONNECTION TO MATING DEVICES

(71) Applicant: AGILENT TECHNOLOGIES, INC., Loveland, CO (US)

(72) Inventors: George P. Walsh, Wilmington, DE (US); Wesley M. Norman, Landenberg, PA (US); Jonathan Michael Frentzel, Wilmington, DE (US); William H. Wilson, Newark, DE (US)

(73) Assignee: Agilent Technologies, Inc., Santa Clara, CA (US)

( * ) Notice: Subject to any disclaimer, the term of this patent is extended or adjusted under 35 U.S.C. 154(b) by 124 days.

(21) Appl. No.: 14/057,016

(22) Filed: Oct. 18, 2013

(65) Prior Publication Data

US 2015/0108749 A1    Apr. 23, 2015

(51) Int. Cl.
*F16L 39/00* (2006.01)
*G01N 30/60* (2006.01)

(52) U.S. Cl.
CPC .................. *G01N 30/6026* (2013.01)

(58) Field of Classification Search
USPC ........ 285/109, 65, 68, 69, 125.1, 25, 62, 63, 285/325, 67, 103
See application file for complete search history.

(56) References Cited

U.S. PATENT DOCUMENTS

| | | | | |
|---|---|---|---|---|
| 640,405 | A | * | 1/1900 | Netter .............................. 285/25 |
| 891,718 | A | * | 6/1908 | McMillan ....................... 285/29 |
| 1,161,641 | A | * | 11/1915 | Engle ......................... 285/148.2 |
| 1,252,660 | A | * | 1/1918 | Clay ............................. 285/317 |
| 1,306,927 | A | * | 6/1919 | Remer et al. .................... 285/25 |
| 3,023,031 | A | * | 2/1962 | Dobrikin ......................... 285/69 |
| 3,581,573 | A | | 6/1971 | Purcell et al. |
| 4,376,641 | A | | 3/1983 | Nestrick et al. |
| 4,532,150 | A | | 7/1985 | Endo et al. |
| 4,938,509 | A | * | 7/1990 | LaPlante ......................... 285/26 |
| 4,985,625 | A | | 1/1991 | Hurst |
| 4,988,870 | A | * | 1/1991 | Diehl ................. G01N 30/7213 250/281 |
| 5,006,315 | A | | 4/1991 | Maroulis et al. |
| 5,338,448 | A | | 8/1994 | Gjerde |
| 5,547,497 | A | | 8/1996 | Klemp et al. |
| 5,567,868 | A | | 10/1996 | Craig et al. |
| 5,686,657 | A | | 11/1997 | Craig et al. |

(Continued)

OTHER PUBLICATIONS

Co-pending U.S. Appl. No. 13/660,273, filed Oct. 5, 2012.

(Continued)

*Primary Examiner* — Aaron Dunwoody (57) ABSTRACT

A representative embodiment is directed to a fitting for fluidically coupling a GC column to another structure. The fitting comprises: a first end configured to receive a ferrule having a tubular element disposed therein, the tubular element being oriented in a first direction; and a second end fluidically connected to the first end and having an opening to provide a fluid from the tubular element in a second direction that is different from the first direction. The second end comprises a substantially planar portion, and the planar portion is configured to make a substantially gas impermeable seal with another element of a GC system.

18 Claims, 6 Drawing Sheets

(56) References Cited

U.S. PATENT DOCUMENTS

| | | |
|---|---|---|
| 5,720,798 A | 2/1998 | Nickerson et al. |
| 5,792,943 A | 8/1998 | Craig |
| 5,888,390 A | 3/1999 | Craig |
| 5,988,703 A | 11/1999 | Craig |
| 5,997,708 A | 12/1999 | Craig |
| 6,089,617 A | 7/2000 | Craig et al. |
| 6,444,326 B1 | 9/2002 | Smith |
| 6,457,236 B1 | 10/2002 | White et al. |
| 6,612,153 B2 | 9/2003 | White et al. |
| 6,679,989 B2 | 1/2004 | Willis et al. |
| 6,709,027 B2 | 3/2004 | Rittenhouse |
| 6,749,749 B2 | 6/2004 | Xie et al. |
| 6,783,871 B2 | 8/2004 | Sheng |
| 6,966,212 B2 | 11/2005 | Klee et al. |
| 7,128,876 B2 | 10/2006 | Yin et al. |
| 7,287,441 B2 | 10/2007 | Klee et al. |
| 7,316,730 B2 | 1/2008 | Rightnour et al. |
| 7,384,457 B2 | 6/2008 | Emmons et al. |
| 7,430,893 B2 | 10/2008 | Grayfer et al. |
| 7,600,439 B1 | 10/2009 | Patterson et al. |
| 7,811,452 B2 | 10/2010 | Yin et al. |
| 8,123,841 B2 | 2/2012 | Masel et al. |
| 8,414,832 B1 | 4/2013 | Roques et al. |
| 2004/0189314 A1* | 9/2004 | Le Foll .................. G01N 27/70 324/464 |
| 2006/0038402 A1 | 2/2006 | Norman et al. |
| 2007/0000828 A1 | 1/2007 | Norman et al. |
| 2007/0029791 A1 | 2/2007 | Haertl |
| 2009/0001008 A1 | 1/2009 | Deorkar et al. |
| 2009/0065415 A1 | 3/2009 | Vetter et al. |
| 2011/0023581 A1 | 2/2011 | Chou et al. |
| 2012/0164026 A1* | 6/2012 | Dehmer .................. B01L 3/021 422/68.1 |
| 2013/0125564 A1 | 5/2013 | Booth |

OTHER PUBLICATIONS

Co-pending U.S. Appl. No. 13/718,061, filed Dec. 18, 2012.
"Deactivated Fused Silica Tubing", Restek Corporation catalog.
Agilent Technologies, Agilent 7890A, "Gas Chromatograph: Maintaining Your GC.", 5th edition, published May 2011.

* cited by examiner

GC COLUMN CONNECTION WITH A PLANAR CONNECTION TO MATING DEVICES

BACKGROUND

Gas chromatography (GC) is used to analyze and detect the presence of many different substances in a gaseous or vaporized sample. The function of a gas chromatograph is to separate the components of a chemical sample and detect the presence and frequently the quantity of those components. The separation is typically accomplished using a capillary column. This column is essentially a piece of fused silica tubing with a coating on the inside that interacts with the sample to separate the components. The most common type of GC column is made from fused silica and has an outside diameter that ranges from 0.700 mm to 0.350 mm.

The GC column must be mated to other components of the GC system, and the mated column must be sealed in such a way that substantially no gas can leak from the environment into the column or into the mating device or from the GC column into the environment.

Many known seals to GC columns are made by compressing a relatively soft material into an enclosed space around the column in such a manner than the material flows radially onto the column outside diameter (thus making a seal) and axially onto tapered surface of the mating device (thus making another seal). In practice, the soft material comes in the form of a ferrule and is made from either polyimide, graphite, blends of these materials, or a very soft metal. This ferrule is compressed by a nut that is rotated so that it is forced to translate axially. This pushes the ferrule along the column and into the tapered enclosed space of the mating device.

As is known, the column extends a certain distance beyond the end of the ferrule. In known GC systems, the end user sets the distance that the column extends beyond the end of the ferrule. In most GC inlets or detectors, the position of the end of the column is very important to the performance of the GC system. This position is determined by the distance of the column end from the ferrule tip. That distance is different for each inlet or detector. Mispositioning of the column by improperly setting the distance of the column end beyond the ferrule can impact the performance of the GC system.

In addition, the column must be trimmed after inserting it through the ferrule because some of the "soft" ferrule material can get into the end of the column, and contaminate the column. Other contamination may be caused from external sources (e.g., when the user's fingers unavoidably contact the ferrule and the end of the column during the installation process). This contamination can further impact the accuracy of the GC system's analysis of a sample.

Furthermore, in known GC systems, a column nut is used to secure the column to the ferrule. Human error in tightening the column nut can impact the performance of the GC column. Under-tightening of the column nut will result in ineffective sealing and the GC system will be prone to teaks. By contrast, over-tightening of the column nut can radially stress the column, causing the column to break, and thereby impacting the seal and performance of the GC system. Recent improvements in the design of soft metal seals reduces this problem, but the end of the column must still be carefully trimmed to the correct length and with a flat cut for proper performance.

What is needed, therefore, is an apparatus that overcomes at least the shortcomings of known structures described above.

BRIEF DESCRIPTION OF THE DRAWINGS

The present teachings are best understood from the following detailed description when read with the accompanying drawing figures. The features are not necessarily drawn to scale. Wherever practical, like reference numerals refer to like features.

DEFINED TERMINOLOGY

It is to be understood that the terminology used herein is for purposes of describing particular embodiments only, and is not intended to be limiting. The defined terms are in addition to the technical and scientific meanings of the defined terms as commonly understood and accepted in the technical field of the present teachings.

As used in the specification and appended claims, the terms 'a', 'an' and 'the' include both singular and plural referents, unless the context clearly dictates otherwise. Thus, for example, 'a device' includes one device and plural devices.

As used in the specification and appended claims, and in addition to their ordinary meanings, the terms 'substantial' or 'substantially' mean to with acceptable limits or degree. For example, 'substantially cancelled' means that one skilled in the art would consider the cancellation to be acceptable.

As used in the specification and the appended claims and in addition to its ordinary meaning, the term 'approximately' means to within an acceptable limit or amount to one having ordinary skill in the art. For example, 'approximately the same' means that one of ordinary skill in the art would consider the items being compared to be the same.

DETAILED DESCRIPTION

In the following detailed description, for purposes of explanation and not limitation, representative embodiments disclosing specific details are set forth in order to provide a thorough understanding of the present teachings. Descriptions of known systems, devices, materials, methods of operation and methods of manufacture may be omitted so as to avoid obscuring the description of the example embodiments. Nonetheless, systems, devices, materials and methods that are within the purview of one of ordinary skill in the art may be used in accordance with the representative embodiments.

A representative embodiment is directed to a fitting for fluidically coupling a GC column to another structure. The fitting comprises: a first end configured to receive a ferrule having a tubular element disposed therein, the tubular element being oriented in a first direction; and a second end fluidically connected to the first end and having an opening to provide a fluid from the tubular element in a second direction that is different from the first direction. The second end comprises a substantially planar portion, and the planar portion is configured to make a substantially gas impermeable seal with another element of a GC system. Among other benefits, the fitting of certain embodiments allows for termination of a GC column to a face-seal with the termination being completed before use by the end user. Beneficially, the present teachings are directed to a fitting that eliminates the need for the end user to make a seal to a fused silica column, and accordingly eliminates the need for the end user to handle ferrules and trim columns to the correct length. The face seal realized by the fittings of representative embodiments ensures effecting seals to the rest of the system more easily and more reliably than known ferrule seals. The other components of the GC system can be designed to use face seals. Where tithes do need to be positioned in an inlet or a detector, the face seals can be designed and made with precisely sized tubing so that the user has no critical adjustments to make.

In another representative embodiment, an apparatus for fluidically coupling a (GC) column to another structure is disclosed. The apparatus comprises: a first fitting, comprising: a first end configured to receive a ferrule having a tubular element disposed therein, the tubular element being oriented in a first direction; a second end fluidically connected to the first end. The second end comprises a first substantially planar portion, the second end comprising an opening to provide a fluid from the tubular element in a second direction that is substantially perpendicular to the first direction. The apparatus further comprises: and a second fitting, comprising: a first end and a second end fluidically connected to the first end, and the second end of the second fitting comprising a second substantially planar portion. The second planar portion of the first fitting is configured to make a substantially gas impermeable seal with the second planar portion of the second fitting.

Figure 1:
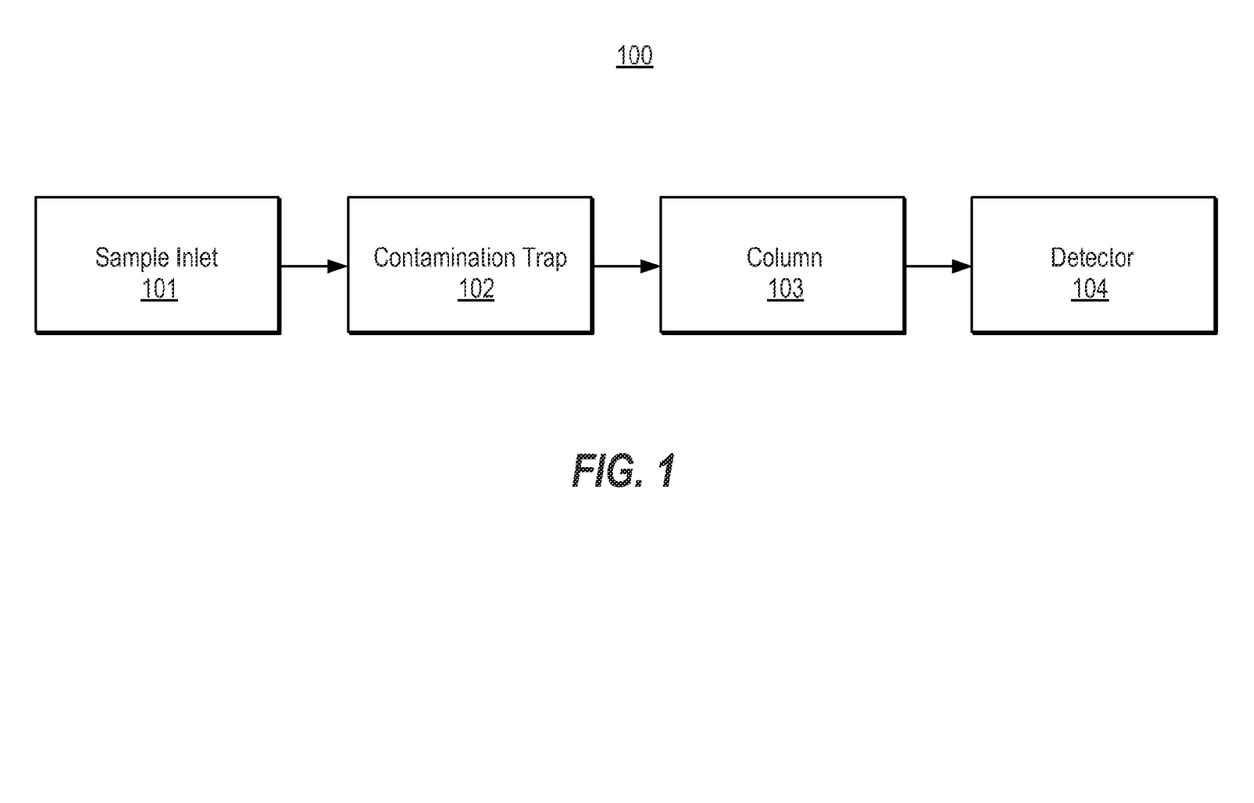
FIG. 1 is a simplified block diagram of a GC system in accordance with a representative embodiment.

As will be appreciated by one having ordinary skill in the art upon review of the present application, among other benefits the fittings of the representative embodiments allow the end user to make connections from a column to other elements of the GC system by a reliable face seal and without needing to handle ferrules or adjust column lengths. FIG. 1 is a simplified block diagram of a GC system 100 in accordance with a representative embodiment. Many aspects of the GC system 100 are known to one of ordinary skill in the art. As such, details of certain known components of the GC system 100 are omitted. In certain instances representative examples of known components that may be implemented are noted, but are presented for illustration and are, in no way, intended to be limiting.

The GC system comprises a sample inlet 101, such as an injection sample inlet. The sample inlet 101 is fluidly coupled to a contaminant trap 102. The contaminant trap 102 is fluidically coupled to a column 103, which may be one of a variety of columns useful in gas chromatography. In an embodiment, the contaminant trap 102 may be as described in concurrently filed, commonly owned U.S. patent application Ser. No. 14/057,022, the disclosure of which is specifically incorporated herein by reference. It is noted that the inclusion of contaminant trap 102 is merely illustrative, and the present teachings are contemplated for use in GC systems that do not comprise a contaminant trap, or that do not comprise a microfluidic contaminant trap as described in the application referenced immediately above.

The column 103 separates the components of a chemical sample. The column 103 may be a capillary column comprising a piece of fused silica tubing (not shown) with a coating on the inner portions of the tubing that interacts with the sample from sample inlet 101 to separate the components of the chemical sample. The dimensions of this column 103 vary, but typical inside diameters range from 100 µm to 530 µm. Typical lengths range from 5 meters to 60 meters. As described in detail below in connection with representative embodiments, the contaminant trap 102 is a microfluidic contaminant trap configured to trap contaminants in the sample from the sample inlet 101 and to prevent the trapped contaminants from reaching the column 103.

The column 103 is connected to a detector 104, which detects the presence and frequently the quantity of the components separated by the column 103. Generally, the detector 104 is a known GC detector such as a flame ionization detector (FID), a mass spectrometer detector (MSD), a thermal conductivity detector (TCD), an electron capture detector (ECD), a nitrogen phosphorus detector (NPD), a sulfur chemiluminescence detector (SCD), a nitrogen chemiluminescence detector (NCD), a pulsed flame photometric detector (PFPD), or a helium ionization detector (HID). In accordance with a representative embodiment, the detector may be a flame photometric detector (FPD) such as described in commonly owned U.S. patent application Ser. No. 13/660,273, filed on Oct. 5, 2012 and entitled "Flame Photometric Detector;" and commonly owned U.S. patent application Ser. No. 13/718,061, filed on Dec. 18, 2012 and entitled "Chemiluminescent Detector having Coating to Reduce Excite Species Adsorption." The disclosures of commonly owned U.S. patent application Ser. No. 13/660,273 and commonly owned U.S. patent application Ser. No. 13/718,061 are specifically incorporated herein by reference. It is emphasized that the use of FPDs is merely illustrative, and many other detectors known to one of ordinary skill in the art are contemplated by the present teachings.

Figure 2A:
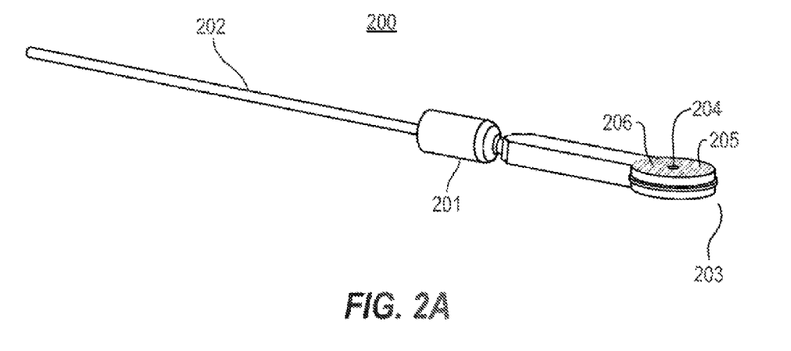
FIG. 2A is perspective view of a fitting in accordance with a representative embodiment.

FIG. 2A is perspective view of a fitting 200 (sometime referred to as first fitting 200 below) in accordance with a representative embodiment. The fitting 200 has a first end 201 configured to receive a ferrule (not shown in FIG. 2A) having a tubular element 202 (sometimes referred to below as first tubular element 202) disposed therein. The tubular element 202 may be a GC capillary column, a metal capillary tube, or other similar component of a GC system that is configured to carry fluid in the GC system. The fitting 200 also comprises a second end 203 that is fluidically connected to the first end 201. The second end 203 comprises an opening 204 (sometimes referred to below as first opening 204) disposed in a substantially planar surface 205 of the fitting 200. As described more fully below, the tubular element 202 is oriented in a first direction, and the opening 204 is oriented to provide fluid from the tubular element 202 in a second direction that is substantially perpendicular to the first direction.

As described more fully below, the substantially planar surface 205 fosters art impermeable gas seal between the fitting 200 and another structure of the GC system. Beneficially, the seal is provided between the substantially planar surface 205 of the fitting to another substantially planar surface through a comparatively straight-forward clamping mechanism or by bonding using a sealant/adhesive material.

In accordance with representative embodiments, the fitting 200 comprises a metal, such as stainless steel. Alternatively, the fitting 200 may comprise one of a variety of nickel alloys, titanium alloys and, for low temperature applications may comprise polymers such as polyimide with suitable coatings. The substantially planar surface 205 is comparatively defect-free and comparatively flat. Illustratively, the substantially planar surface 205 has a matte finish with surface roughness (Ra) of approximately 0.4 μm or less. Additionally, the substantially planar surface 205 is conducive to sealing to another substantially planar surface, such as described below. In certain embodiments, the seal can be improved, or imperfections in the substantially planar surface 205 can be remedied by application of a "soft" or pliable layer 206 over the substantially planar surface 205 and surrounding the opening 204. In a representative embodiment, the pliable layer 206 comprises a soft metal, such as gold or silver having a thickness of approximately 6.0 μm. In certain embodiments, the pliable layer 206 allows for the formation of a substantially impermeable gas seal between the fitting 200 and another structure of the GC system at a reduced clamping or compression force compared to fittings without the pliable layer 206. Care must be taken in the selection of the material and process of forming the pliable layer 206 to avoid or remove contaminants, and to avoid compromising deactivation coatings that may be used.

Figure 2B:
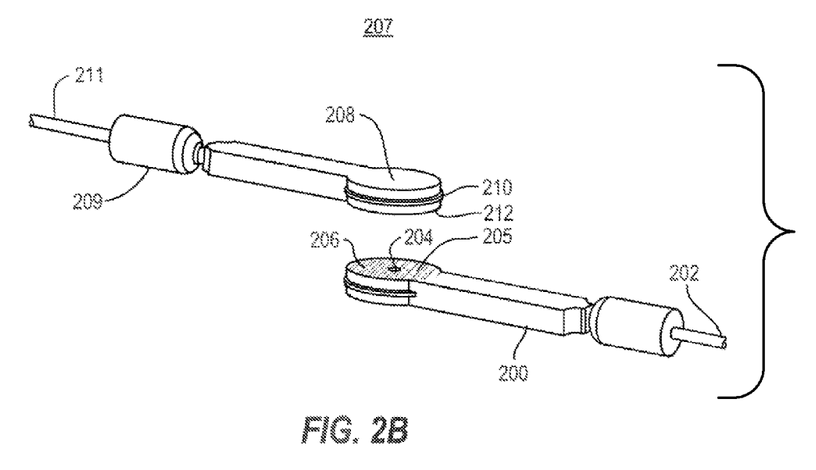
FIG. 2B is a perspective view of an apparatus comprising two fittings in accordance with a representative embodiment.

FIG. 2B is a perspective view of an apparatus 207 comprising first fitting 200 and a second fitting 208 in accordance with a representative embodiment. FIG. 2B shows the first and second fittings 200, 208 prior to being brought in contact with one another so that certain aspects of the apparatus 207 can be more easily described.

The second fitting 208 comprises a first end 209 and a second end 210, and the second end 210 is fluidically connected to the first end 209. A tubular element 211 (sometimes referred to below as second tubular element 211) is disposed in the first end 209. The second tubular element 211 may be a GC column, or other similar component of a GC system that is configured to provide fluid in the GC system. The second tubular element 211 is oriented in a first direction, and the opening in the substantially planar portion 212 is oriented to provide fluid from the tubular element 211 in a second direction that is substantially perpendicular to the first direction.

The second end 210 comprises an opening (not shown in FIG. 2B) disposed in a substantially planar portion 212 (sometimes referred to as the second substantially planar portion 212) of the second fitting 208. Like first fitting 200, second fitting 208 may have a pliable layer (not shown) disposed over the second substantially planar portion 212 and around the opening to foster a suitable seal at a comparatively reduced clamping/compressive force.

As depicted in FIG. 2B, the first substantially planar surface 205 and opening 204 of the first fitting 200 opposes the second substantially planar portion 212 and the opening (not shown) of the second fitting. Upon contacting the first substantially planar surface 205 with the second substantially planar portion 12, a face-seal of the first opening 204 and the second opening may be realized upon application of a clamping/compressive force to the first and second fittings 200, 208. As such, a fluid flowing in a first direction in first tubular element 202 is flowed in a second direction substantially perpendicular to the first direction by the first fitting 200, and from this second direction the fluid is flowed in a third direction that is substantially perpendicular to the second direction and parallel to the first direction. As such, the apparatus 207 allows for a vertical translation of fluid flowing in the first tubular element 202 to the second tubular element 211.

Figure 3:
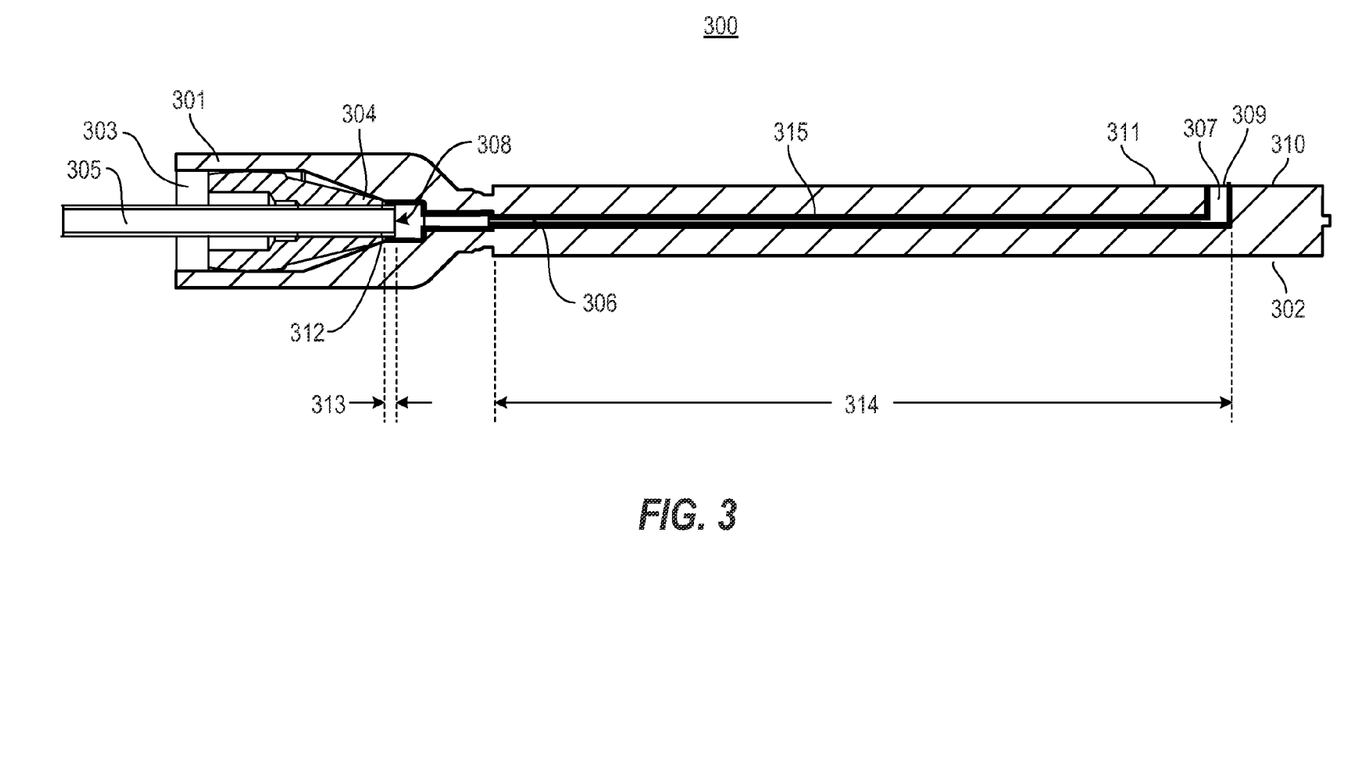
FIG. 3 is a cross-sectional view of a fitting in accordance with a representative embodiment.

FIG. 3 is a cross-sectional view of a fitting 300 in accordance with a representative embodiment. Many aspects of the fitting 300 are common to first and second fittings 200, 208 described above. Notably, many of the details of the materials, structure, features, dimensions and methods of fabrication described above in connection with the representative embodiments of FIG. 2A~2B are common to the description of the representative embodiments of FIG. 3. Often, these details are not repeated in order to avoid obscuring the description of the representative embodiment of FIG. 3. Finally, the connection provided by the fitting 300 is illustratively to a GC column. It is emphasized that this is merely illustrative, and that other tubular elements commonly used in a GC system may be used, such as a GC capillary column, a metal capillary tube, or other similar components that are configured to carry fluid in the GC system.

The fitting 300 comprises a first end 301 and a second end 302. The first end 301 comprises a cavity 303 that is configured to receive a ferrule 304 that has a GC column 305 disposed therein. In representative embodiments, the ferrule 304 is press fit into the cavity 303 and is retained therein. The press fit could be designed following industry standard guidelines, for example, an ANSI H7/s6 fit is specified for retaining the ferrule 304 in the fitting 300. Alternatively, the ferrule 304 may be adhered in the cavity by a suitable adhesive material or by welding (e.g., laser welding). Finally, if instead of the GC column 305, a metal capillary was being connected via fitting 300, welding or brazing may be useful to secure the metal capillary to the fitting, and the ferrule 304 could be foregone.

The fitting 300 has a first channel 306 oriented in a first direction, and a second channel 307 oriented in a second direction that is substantially perpendicular to the first direction as shown. The first channel 306 is fluidically connected to an end 308 of the GC column 305, and an opening 309 is fluidically connected to the second channel 307. The opening 309 is provided in a substantially planar portion 310 of the fitting 300. The planar portion 310 may also comprise a pliable layer 311 disposed around the opening 309 to foster formation of a substantially impermeable gas seal between the fitting 300 and another structure of the GC system at a reduced clamping or compression force compared to fittings without the pliable layer 311.

During operation, fluid from the GC column 305 flows in the first direction and emerges from the opening 309 in a second direction that is substantially perpendicular to the first direction. As described above in connection with representative embodiments of FIG. 2B, the substantially planar portion 310 of the fitting 300 is configured to form a face-seal with another substantially planar surface (e.g., a substantially planar portion of another fitting (e.g., second fitting 208, or of a planar component of a microfluidic device (not shown in FIG. 3)).

The cavity 303, and the first and second channels 306, 307, as well as other features of the fitting 300 can be formed using known methods based on the materials selected for the fitting. These connections many be implemented as described in commonly owned U.S. Pat. Nos. 5,792,943, 5,686,657, 5,567,868, 7,128,876 and 7,811,452, and as described in U.S. Pat. No. 8,123,841. The disclosures of these U.S. patents are specifically incorporated herein by reference.

As depicted in FIG. 3, the end 308 of the GC column 305 extends beyond an end 312 of the ferrule 304 by a distance 313. The distance 313 is set so that the GC column 305 is not too long or too short for the fitting 300 that the ferrule 304 is not swaged too close to end 308 to avoid cracking of the GC column 305 and that the necessary void is suitably and rapidly flushed and well swept. As depicted in FIG. 3, the fitting 300 comprises a length 314 along which the first channel extends. This length 314 is provided to allow for a significant thermal break between one end of the fitting (e.g., first end 301) and the other end of the fitting (e.g., second end 302). In this way, the one end of the fitting can be maintained at a comparatively high temperature while the opposing end can be at a comparatively low temperature (e.g., the temperature experienced by the portions of the column not in thermal contact with the inlet or the detector). By contrast, without this thermal break, if the column end remains at the comparatively high temperature found on a detector or inlet, the lifetime of the column end will be much shorter than the lifetime of rest of the column tubing. Beneficially, and among other benefits, the thermal break provided by length 314 allows the column ends to be cool enough to have essentially the same lifetime as the column tithing will have. The length 314 depends on the thermal environment where the fitting 300 is implemented. For purposes of illustration, the length 314 is between approximately 20 mm to approximately 25 mm for a particular thermal environment.

In accordance with a representative embodiment, a coating 315 is applied to all surfaces of the fitting 300 that come in contact with the sample. The coating 315 is a deactivation coating that may be applied, for example, over the surfaces of the first and second channels 306, 307 that come into contact with the sample to reduce the interaction of analytes of the sample with the surfaces with which the sample contacts. The coating 315 comprises a selected chemical substance useful in reducing the interaction of the surface with analytes of interest within the sample. In a representative embodiment, the coating 315 comprises a functionalized hydrogenated amorphous silicon surface, such as described, for example in U.S. Pat. No. 6,444,326, to Smith. The disclosure of U.S. Pat. No. 6,444,326 is specifically incorporated herein by reference. In a second representative embodiment, the coating 315 comprises a silicon carbide surface, such as described, for example in U.S. Pat. No. 4,532,150, to Endo et al. The disclosure of U.S. Pat. No. 4,532,150 is specifically incorporated herein by reference. In a third representative embodiment, the coating 315 comprises a siloxane surface, such as described, for example in U.S. Pat. No. 4,376,641, to Nestrick, et al. The disclosure of U.S. Pat. No. 4,376,641 is specifically incorporated herein by reference. Illustratively, the coating 315 may be a known silicon-based coating, a known siloxane, and other known polymeric, monomeric, or carbide coatings. The coating is applied by known methods, and is applied after various components of the fitting are bonded to one another to ensure all surfaces that come into contact with the analytes of the sample are properly coated.

Figure 4:
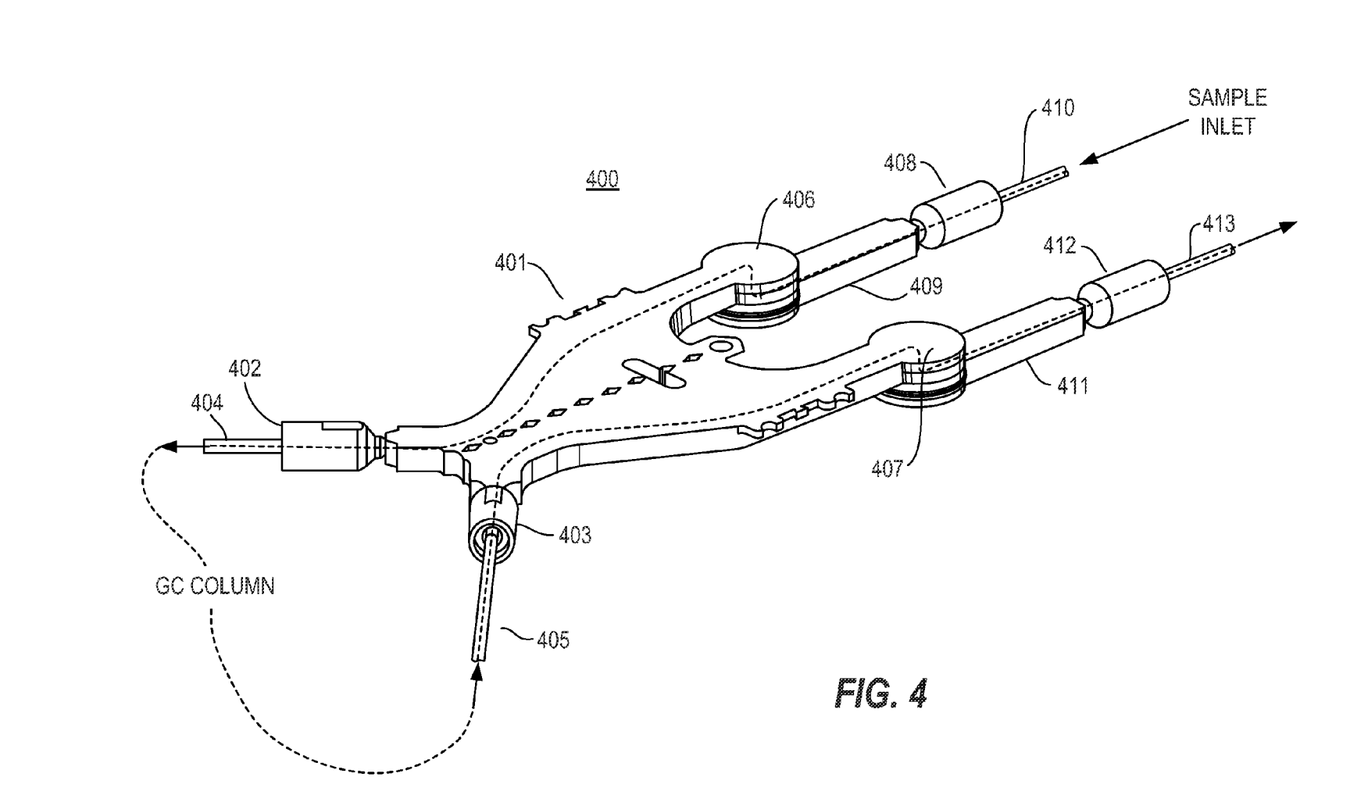
FIG. 4 is a perspective view of a fitting in accordance with a representative embodiment.

FIG. 4 is a perspective view of an apparatus 400 in accordance with a representative embodiment. Many aspects of the apparatus 400 are common to fittings of representative embodiments described above. Notably, many of the details of the materials, structure, features, dimensions and methods of fabrication described above in connection with the representative embodiments of FIG. 2A~3 are common to the description of the representative embodiments of FIG. 4. Often, these details are not repeated in order to avoid obscuring the description of the representative embodiment of FIG. 4. Finally, it is noted that the fluid paths depicted and described in connection with a representative embodiment below are merely illustrative. Other fluid paths for effecting different connections (e.g., cross-connections) are contemplated by the present teachings.

The apparatus 400 is configured to receive fluid (e.g., from an outlet of a sample inlet) and route the fluid through a portion of a GC system (not shown). For example, the apparatus 400 may be used to accept a sample from a contaminant trap (not shown) such as the microfluidic contaminant trap of above-referenced application.

The apparatus 400 comprises a body 401 that includes microfluidic channels (not shown) that make fluidic connections between components described below. The microfluidic channels may be formed using known methods, such as etching methods noted above. The apparatus further comprises a first fitting 409 and a second fitting 411. The first and second fittings 409, 411 may be fittings described above in connection with representative embodiments of FIGS. 2A~3 configured to make face-seals as described below.

The body 401 comprises a first element 402 and a second element 403 configured to seal first capillary 404 and second capillary 405, respectively in the manner of the first end 201 of fitting 200 in FIG. 2A. The body 401 also comprises a third element 406 and a fourth element 407 that are configured to make a face seal to other system components in the same way that the second end 203 of fitting 200 in FIG. 2A makes connections to other system components. The body 401 contains a first channel (not shown) fluidically connecting first element 402 to third element 406 and a second channel (not shown) fluidically connecting second element 403 to fourth element 407. As such, body 401 comprises components and is configured to function in the manner of two of the fittings of representative embodiments described in connection with FIGS. 2A-3 incorporated into a single structure, body 401.

In apparatus 400, a first connection 408 of a first fitting 409 receives fluid from a third capillary 410 (e.g., the outlet from a sample inlet). The fluid travels (along a path indicated by a dashed line in FIG. 4) through a microfluidic channel (not shown) to the end of first fitting 409. The first fitting 409 provides a face-seal to the third element 406 of body 401. The first fitting 409 provides fluidic communication (as indicated by the dotted line) to the third element 406 of body 401. The fluid continues through the first microfluidic channel in body 401 to first element 402 which is fluidically connected to first capillary 404, which is illustratively the GC column or other component (not shown) of the GC system. After traversing the GC column or other component, the fluid travels via second capillary 405 to second element 403 of the body 401. The fluid travels through the second microfluidic channel of body 401 (not shown) to the fourth element 407 of body 401. The fourth element 407 is connected to the second fitting 411-via a face-seal. The first and second fittings 409, 411 each may be a fitting described above in connection with representative embodiments of FIGS. 2A~3 configured to make face-seals as described above. The second fitting 411 is fluidically connected via a second connection 412, to a fourth capillary 413.

Figure 5:
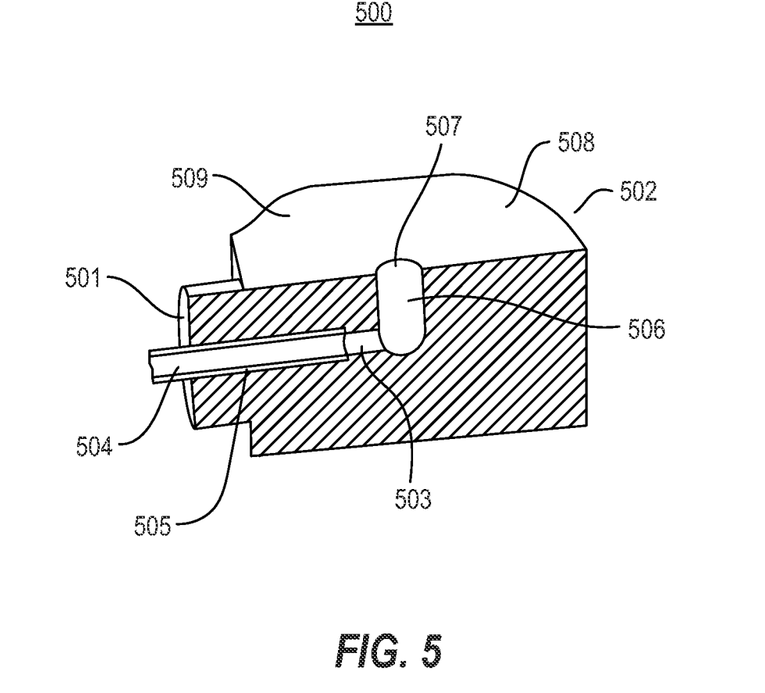
FIG. 5 is a cross-sectional view of a fitting in accordance with a representative embodiment.

FIG. 5 is a cross-sectional view of a fitting 500 in accordance with a representative embodiment. Many aspects of the fitting 500 are common to 200, 208, 300 and 400 described above. Notably, many of the details of the materials, structure, features, dimensions and methods of fabrication described above in connection with the representative embodiments of FIG. 2A~4 are common to the description of the representative embodiments of FIG. 5. Often, these details are not repeated in order to avoid obscuring the description of the representative embodiment of FIG. 5.

The fitting 500 comprises a first end 501 and a second end 502. The first end 501 comprises a first channel 503 that is configured to receive a GC column 504. In the representative embodiment, the GC column 504 is secured and sealed in the first channel 503 using a binder material 505 that is applied around the outer portion e.g., around the circumference) of the GC column 504. The binder material 505 fosters adhesion between the GC column 504 and the first channel 503, and thus between the GC column 504 and the fitting 500. In accordance with representative embodiments, the binder material 505 may comprise a suitable uncured polyimide resin or a suitable alkali-metal silicate with a cross-linking agent. It is emphasized that other binder materials useful to secure and seal the GC column 504 to the first channel 503 within the purview of one of ordinary skill in the art may be used.

The first channel 503 oriented in a first direction, and the fitting 500 comprises a second channel 506 oriented in a second direction that is substantially perpendicular to the first direction as shown. The first channel 503 is fluidically connected to the second channel 506, which is fluidly connected to an opening 507 of the fitting 500. The opening 507 is provided in a substantially planar portion 508 of the fitting 500. The planar portion 508 may have a pliable layer 509 disposed around the opening 507 to foster formation of a substantially impermeable gas seal between the fitting 500 and another structure of the GC system at a reduced clamping or compression force compared to fittings without the pliable layer 509.

During operation, fluid from the GC column 504 flows in the first direction in the first channel 503, through the second channel 506 and emerges from the opening 507 in a second direction that is substantially perpendicular to the first direction. As described above in connection with representative embodiments of FIGS. 2B and 3, the substantially planar portion 508 of the fitting 500 is configured to form a face-seal with another substantially planar surface (e.g., a substantially planar portion of another fitting (e.g., second fitting 208, or of a planar component of a microfluidic device (not shown in FIG. 5))).

The first and second channels 503, 506, as well as other features of the fitting 500 can be formed using known methods based on the materials selected for the fitting. These connections many be implemented as described in above referenced commonly owned U.S. Pat. No. 5,792,943, 5,686,657, 5,567,868, 7,128,876 and 7,811,452, and as described in U.S. Pat. No. 8,123,841.

Figure 6:
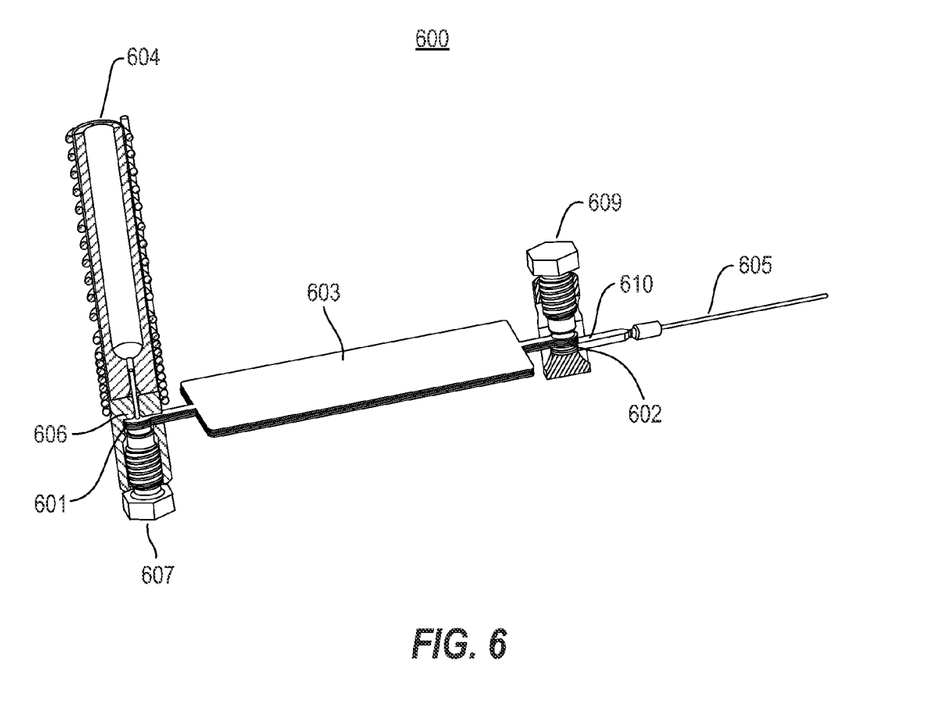
FIG. 6 is a perspective view of a microfluidic device coupled to a GC column using fittings in accordance with a representative embodiment.

FIG. 6 is a perspective view of an apparatus 600 comprising a first flat surface 601 and a second flat surface 602 that couple a microfluidic device 603 between a flat surface on a GC sample inlet 604 and a flat surface of a fitting in accordance with a representative embodiment connected to GC column 605 using compression of the mating flat surface to create face seals. Many aspects of the apparatus 600 are common the embodiments described above, and the fittings may be one or more of the fittings 200, 300 and 500 described above. Notably, many of the details of the materials, structure, features, dimensions and methods of fabrication described above in connection with the representative embodiments of FIG. 2A~5 are common to the description of the representative embodiments of FIG. 6. Often, these details are not repeated in order to avoid obscuring the description of the representative embodiment of FIG. 6.

In accordance with a representative embodiment, the microfluidic device 603 is a microfluidic contaminant trap such as described in concurrently filed, commonly owned U.S. patent application Ser. No. 14/057,022, referenced above. It is emphasized, however, that this is merely illustrative, and that other microfluidic devices known to one of ordinary skill in the art may be provided between two components of a GC system. Illustratively, the microfluidic device 603 may be a microfluidic device such as described in U.S. Pat. No. 5,792,943. As can be appreciated from a review of the description the embodiments of FIG. 6, the first and second flat surface 601, 602 usefully provide a substantially impermeable gas seal between components that are substantially cylindrical by providing a face seal between the components and the microfluidic device 603.

The first flat surface 601 of microfluidic device 603 is compressed against a substantially flat surface 606 at the bottom of GC sample inlet 604 by a first sealing screw 607 to form the substantially impermeable gas seal.

The second flat surface 602 of a microfluidic device 603 is compressed against a substantially flat surface at the fitting 610 by a second sealing screw 609 to form the substantially impermeable gas seal.

It is noted that the use of the first seating screw 607 and the second sealing screw 609 is merely illustrative, and other devices within the purview of one of ordinary skill in the art may be used to provide a compressive/clamping force between the substantially planar portion (not shown in FIG. 6) of the first flat surface 601 of the microfluidic device 603 and the substantially flat surface 606, and between the second flat surface 602 and the substantially flat surface at the fitting 610. Alternatively, as noted above, rather than using first seating screw 607, or the second sealing screw 609, or both, the substantially impermeable gas seals between the substantially planar portions (not shown in FIG. 6) of the first flat surface 601 and the second flat surface 602, and the substantially flat surface at the substantially flat surface 606 and the substantially flat surface at the fitting 610 may be effected using a bonding method such as with a suitable adhesive/sealing material or by laser welding.

During operation, fluid from the GC sample inlet 604 flows in a first direction and emerges from the first flat surface 601 in a second direction that is substantially perpendicular to the first direction. The fluid then flows in the second direction through the microfluidic device 603 to the second flat surface 602, emerging from the second flat surface 602 in a third direction and enters fitting 610. The fluid then flows through fitting 610 to the GC column 605.

In view of this disclosure it is noted that the methods and devices can be implemented in keeping with the present teachings. Further, the various components, materials, structures and parameters are included by way of illustration and example only and not in any limiting sense. In view of this disclosure, the present teachings can be implemented in other applications and components, materials, structures and equipment needed to implement these applications can be determined, while remaining within the scope of the appended claims.

The invention claimed is:

1. A fitting for fluidically coupling a gas chromatography (GC) column to another structure, the fitting comprising:
   a GC column comprising a tubular element;
   a first end that receives a ferrule haying the tubular element disposed therein, the tubular element being oriented in a first direction; and
   a second end fluidically connected to the first end and having an opening oriented in a second direction that is different than the first direction, the second end comprising a substantially planar portion; and a channel between the first end and the second end, and a coating is disposed over the channel, wherein the coating reduces interactions of analytes with the channel.

2. A fitting as claimed in claim 1, wherein the ferrule is press-fit into the first end of the fitting.

3. A fitting as claimed in claim 1, wherein the second direction is substantially perpendicular to the first direction.

4. A fitting as claimed in claim 3, wherein the fitting comprises a first material and a coating disposed over the planar portion.

5. A fitting as claimed in claim 4, wherein the coating fosters the substantially gas impermeable seal.

6. A fitting as claimed in claim 1, wherein the tubular element extends beyond an end of the ferrule.

7. A fitting as claimed in claim 1, further comprising a pliable layer over the substantially planar portion.

8. A fitting as claimed in claim 1, wherein the fitting further comprises:
    a cavity at the first end receiving the ferrule and oriented, in the first direction;
    a first channel oriented in the first direction and fluidly connected to the first end;
    a second channel oriented in the second direction and fluidly connected to the first channel and the opening; and
    a pliable layer disposed around the opening.

9. An apparatus comprising the fitting of claim 1, and comprising a GC detector connection, or a GC inlet connection, or GC flowpath device, as the other structure fluidly coupled to the GC column.

10. An apparatus according to claim 9, comprising the fitting of claim 1 and another element of a GC system, wherein the substantially planar surface of the fitting makes a substantially gas impermeable seal with the other element of the GC system.

11. An apparatus for fluidically coupling a gas chromatography (GC) column to another structure, the apparatus comprising:
    a first fitting, comprising: a first end that receives a ferrule having a tubular element disposed therein, the tubular element being oriented in a first direction a second end fluidically connected to the first end, the second end comprising a first substantially planar portion, the second end comprising an opening oriented in a second direction that is substantially perpendicular to the first direction; and
    a second fitting, comprising: a first end and a second end fluidically connected to the first end, the second end of the second fitting comprising a second substantially planar portion, wherein the first substantially planar portion of the first fitting makes a substantially gas impermeable face-seal with the second substantially planar portion of the second fitting.

12. An apparatus as claimed in claim 11, wherein the ferrule is a first ferrule, the tubular element is a first tubular element, and the second fitting receives a second ferrule having a second tubular element disposed therein, the first and second tubular elements being oriented in the first direction.

13. An apparatus as claimed in claim 12, wherein the first ferrule is press-fit into the first end of the fitting.

14. An apparatus as claimed in claim 12, wherein the first fitting comprises a first material and a coating disposed over the first substantially planar portion.

15. An apparatus as claimed in claim 14, wherein the coating fosters the substantially gas impermeable seal.

16. The apparatus of claim 11, wherein the tubular element is a GC capillary column and the first end of the second fitting is fluidically coupled to another element of a GC system.

17. An apparatus for fluidically coupling a gas chromatography (GC) column to another structure, the apparatus comprising:
    a body comprising: a first element; a second element, a third element and a fourth element, and a first channel and a second channel, wherein the third element and the fourth element each comprise a substantially planar portion and an opening in a substantially planar portion, and
    wherein the first channel connects the first and third elements, and the second channel connects the second and fourth elements.

18. An apparatus as claimed in claim 17, further comprising a GC column, wherein the GC column is connected between the first element and the second element.

* * * * *

UNITED STATES PATENT AND TRADEMARK OFFICE
CERTIFICATE OF CORRECTION

PATENT NO. : 9,638,676 B2
APPLICATION NO. : 14/057016
DATED : May 2, 2017
INVENTOR(S) : George P. Walsh et al.

It is certified that error appears in the above-identified patent and that said Letters Patent is hereby corrected as shown below:

In the Specification

In Column 4, Line 62, delete "art" and insert -- an --, therefor.

In Column 5, Line 59, delete "12," and insert -- 212, --, therefor.

In Column 6, Line 10, delete "FIG. 2A~2B" and insert -- FIGS. 2A-2B --, therefor.

In Column 6, Line 62, delete "many" and insert -- may --, therefor.

In Column 7, Line 65, delete "FIG. 2A~3" and insert -- FIGS. 2A-3 --, therefor.

In Column 8, Line 20, delete "FIGS. 2A~3" and insert -- FIGS. 2A-3 --, therefor.

In Column 8, Line 55, delete "411-via" and insert -- 411 via --, therefor.

In Column 8, Line 58, delete "FIGS. 2A~3" and insert -- FIGS. 2A-3 --, therefor.

In Column 8, Line 67, delete "FIG. 2A~4" and insert -- FIGS. 2A-4 --, therefor.

In Column 9, Line 64, delete "FIG. 2A~5" and insert -- FIGS. 2A-5 --, therefor.

In the Claims

In Column 10, Line 63, in Claim 1, delete "haying" and insert -- having --, therefor.

In Column 11, Line 22, in Claim 8, delete "oriented," and insert -- oriented --, therefor.

Signed and Sealed this
Fourth Day of July, 2017

Joseph Matal
*Performing the Functions and Duties of the
Under Secretary of Commerce for Intellectual Property and
Director of the United States Patent and Trademark Office*

CERTIFICATE OF CORRECTION (continued)
U.S. Pat. No. 9,638,676 B2

In Column 11, Line 44, in Claim 11, delete "direction" and insert -- direction; --, therefor.

In Column 12, Line 26, in Claim 16, delete "column" and insert -- column, --, therefor.

In Column 12, Line 33, in Claim 17, delete "element;" and insert -- element, --, therefor.